(12) United States Patent
Westendorf

(10) Patent No.: US 6,270,510 B1
(45) Date of Patent: Aug. 7, 2001

(54) NOSTRIL GROOMING TOOL

(76) Inventor: Marlene Westendorf, 115 Kari Glen Way, Fayetteville, GA (US) 30215

( * ) Notice: Subject to any disclaimer, the term of this patent is extended or adjusted under 35 U.S.C. 154(b) by 0 days.

(21) Appl. No.: 09/453,181

(22) Filed: Dec. 2, 1999

(51) Int. Cl.$^7$ ................................................ A61F 11/00
(52) U.S. Cl. ............................................................ 606/162
(58) Field of Search ................................. 606/162; 604/1; 15/118, 209.1, 225, 210.1

(56) References Cited

U.S. PATENT DOCUMENTS

| | | |
|---|---|---|
| 1,326,616 | 12/1919 | Schuler . |
| 2,096,162 | 10/1937 | Daley . |
| 2,691,985 * | 10/1954 | Newson ................................ 604/1 X |
| 3,203,418 | 8/1965 | Johnston . |
| 4,457,756 * | 7/1984 | Kern et al. ............................ 604/1 X |
| 5,214,821 | 6/1993 | Burrow et al. . |
| 5,715,559 | 2/1998 | Mitri . |
| 5,816,241 | 10/1998 | Cook . |
| 5,895,408 * | 4/1999 | Pagan .................................. 606/199 |

* cited by examiner

Primary Examiner—Olik Chaudhuri
Assistant Examiner—Hoa B. Trinh
(74) Attorney, Agent, or Firm—Robert N. Blackmon

(57) ABSTRACT

A device for dislodging and removing mucositys from the nostril of the user. The device consists of an elongated body made of waxed paper or twisted paper or similar material. The central portion is padded and the two distal ends also have discrete padded areas. The device in use is folded over to present a doubled-over padded section of considerable thickness. The two ends have slightly raised loops (angled above the longitudinal axis) to form padded scoops. The scoops may be hollow to form an eyelet or may be closed to form pads or spoons.

10 Claims, 2 Drawing Sheets

NOSTRIL GROOMING TOOL

BACKGROUND OF THE INVENTION

1. Field of the Invention

The present invention relates to a device for cleaning the inner nasal cavities of mucous particles.

2. Description of the Prior Art

It is a common everyday problem that the nasal passages ("nose") continues to build up mucous particles ("mucositys") creating a nuisance and making breathing through the nose difficult. This is especially true among sufferers of hayfever and other allergies. In order to clear the nose, the choices that an individual has include blowing one's nose into a handkerchief or similar device, or one can "pick" one's nose by inserting a finger or implement into the nasal passage to unblock the nasal passage. The former method is often ineffective and the latter method has its inherent difficulties and dangers by the size or sharpness of the chosen implement, often resulting in damage to the nasal cavity.

U.S. Pat. No. 3,923,061 to Rossignol issued Dec. 2, 1975, shows a padded tool having a rigid body for manipulating the tool into a body cavity for cleaning.

U.S. Pat. No. 3,626,946 to Messey issued Dec. 14, 1971, shows a cigar shaped cleaner of a non-woven fabric for cleaning the ear of a user.

Neither of the above inventions and patents, taken either singly or in combination, is seen to describe the instant invention as claimed.

SUMMARY OF THE INVENTION

Accordingly, it is a principal object of the invention to provide an improved device for cleaning the nasal passages which does not suffer the disadvantages of the prior art devices.

It is another object of the invention to provide a nostril cleaning tool that is padded to protect the interior lining of the nasal cavity.

It is a further object of the invention to provide a nostril cleaning tool having a semi-rigid shaft for manipulating the padded portions deftly into the interior reaches of the nasal cavity.

Still another object of the invention is to provide a nostril cleaning tool having multiple padded portions of various sizes for cleaning different portions of the nasal cavity.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT(S)

The present invention is directed to a novel device for cleaning the interior passages of the nose with a padded implement having variously shaped ends for cleaning different parts of the nasal cavities.

Figure 1:
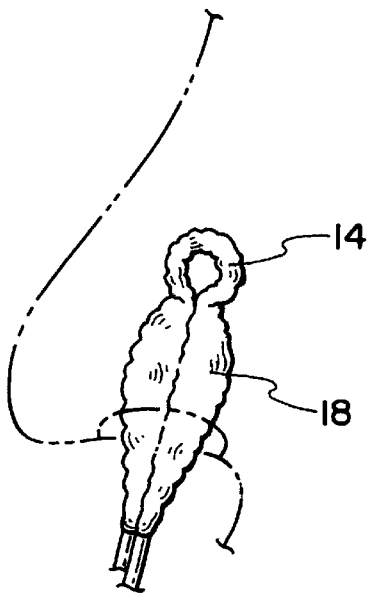
FIG. 1 is a side environmental view of one end of a nostril cleaning tool inserted into the nasal cavity of a user.
Figure 2:
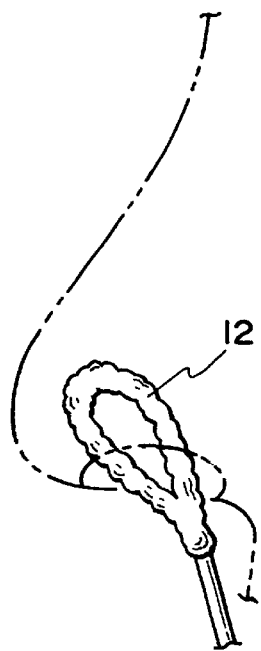
FIGS. 2 and 3 are side environmental views of the nostril cleaning tool inserted into different areas of the nasal cavity.
Figure 3:
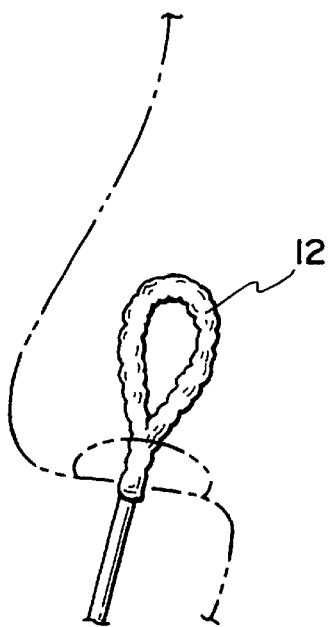
Figure 4:
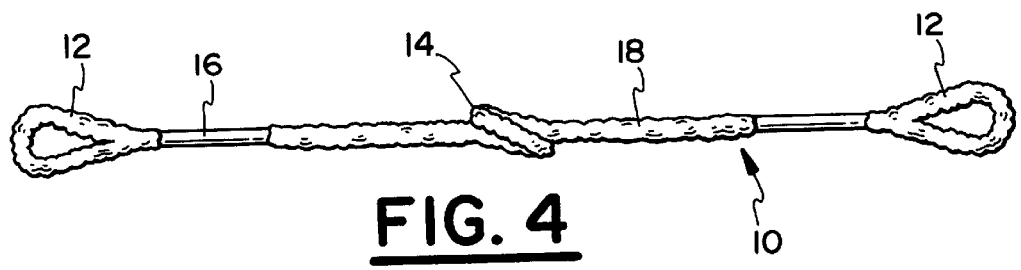
FIG. 4 is a top plan view of the nostril cleaning tool according to the present invention.
Figure 5:
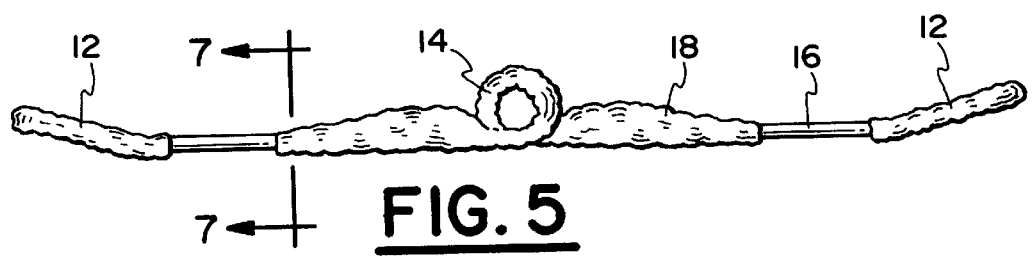
FIG. 5 is a side perspective view of the nostril cleaning tool according to the present invention.

As shown in FIGS. 1–3, the nostril cleaning tool has variously shaped padded areas of the cleaner to clean various areas of the nostril. As best seen in FIGS. 4 & 5, the cleaner 10 has two distal ends terminating in loops ("eyelets") 12 covered by padding. Each loop in a preferred embodiment is one half inch wide at its widest point and approximated ⅞ inch from the start of the padding to the farthest end of the loop. The padding can be made of a cotton material, a woven material, or a non-woven fabric, depending on the end use and current cost of each. The padding may be made of an absorbent material and have a "waffle" pattern or overlay pattern to trap water, mucous, mucositys and the like and maintain its structure. The loops 12 are also slightly angled outwardly from the central axis of the elongated body 16 to provide for better reach. The end of the loop 12 is raised approximately one quarter to one half inch from the central axis of the body 16.

Figure 8:
FIG. 8 shows a second embodiment of the padded portion of the cleaner having material covering the eyelet of the cleaner end.

In the preferred embodiment the loops 12 are hollow forming an eyelet to capture mucous particles in the loop. In a second embodiment shown in FIG. 8, the loop can be completely covered by a fabric material 20 to form a pad for cleaning the nose.

The central portion in both embodiments has a loop 14 centrally located along the elongated body 16. A significant portion of the central length of the body 16 including loop 14 is covered by a padded section 18. The loop is approximately one half inch tall and ⅜ inch wide at its widest section in a preferred embodiment, and it has been found that the padded section should preferably be approximately 1½ inches long.

Figure 6:
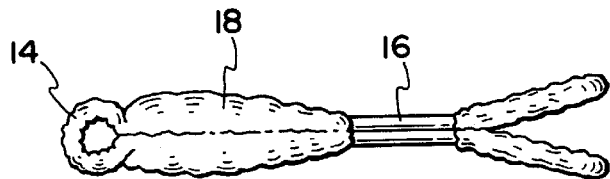
FIG. 6 is a side perspective view of the nostril cleaning tool folded in half to form a dual-ended cleaner.
Figure 7:
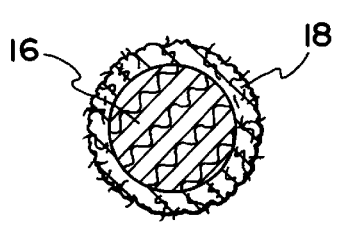
FIG. 7 shows a cross section of a padded portion of the cleaner according to the present invention.

In operation, the tool is folded in half as shown in FIG. 6. This presents a second end having a loop 14 with an extended length of padded section 18 covering the loop 14 and a portion of the body 16. The padded section is preferably tapered from the loop towards the end, from a folded height of ⅝ inch To clean one's nose according to the present invention, a user blows his nose into a tissue to clear the majority of mucous from the nasal cavity and to bring deeper mucous into the forward nasal cavity. The nostril cleaning tool ("grooming tool") is then bent in half as described above to bring the two opposing ends together. The padded section formed by loop 14 and pad 18 is inserted into the nasal cavity next (FIG. 1). The large padded area and large loop section can then be rotated ("twisted") within the nose to remove mucous from the walls and center of the nostrils. The loop 14 will also capture mucous from the back of the nasal cavity as it reaches farther than the padded section 18. The tool is then opened to present one of the two spoon shaped loops 12 into the nostril. The spoons are designed to scoop out the harder to reach areas of the nostril. The first spoon is used to clean the forward corner pocket of the nostril (FIG. 3), and the second spoon is used to clean the closer reaches of the nostril wall of any remaining debris. A second grooming tool is then used to clean the second nostril.

It is to be understood that the present invention is not limited to the sole embodiment described above, but encompasses any and all embodiments within the scope of the following claims.

I claim:

1. A nostril cleaning device comprising an elongated body having a central portion and distal ends; and further having discrete padding sections covering both of said distal ends and a central padding section covering said central portion of said elongated body, wherein at least one of said distal end padding sections is formed in a loop to define an eyelet.

2. The nostril cleaning device of claim 1, wherein said central portion covered by said central padding section has a section defining a loop therein.

3. The nostril cleaning device of claim 1, wherein said device is folded in half to form a doubled-over, padded cleaning section at said central portion.

4. The nostril cleaning device of claim 1, wherein said padding sections is made of an absorbent material having a waffle pattern.

5. The nostril cleaning device of claim 1, wherein said elongated body is made of a waxed paper to add rigidity to the elongated body.

6. The nostril cleaning device of claim 1, wherein said elongated body is made of a twisted paper to add rigidity to the elongated body.

7. The nostril cleaning device of claim 1 wherein said at least one distal end padding loop is angled away from a longitudinal axis of the elongated body.

8. A method of cleaning a nasal cavity of a person, comprising the steps of:

a) providing an elongated body having a central padded portion and first and second distal ends, each of said distal ends being padded;

b) bending said elongated body in half about said central padded portion to form a nostril cleaning tool;

c) placing said doubled-over central portion in a nasal cavity of a person to clean the nasal passage of mucous particles;

d) placing said first distal end in a nasal cavity to scrape additional mucous particles out of a nose;

e) placing said second distal end in a nasal cavity to scrape additional mucous particles out of a nose.

9. The method according to claim 8, further comprising the steps of:

f) providing said first distal end with a loop forming an eyelet for cleaning a nasal passage.

10. A nostril cleaning device having a) an elongated body having two distal ends;

b) each of said two distal ends covered by a padding material;

c) a central loop formed along a central portion of said elongated body and covered by a padded material;

d) each of said distal ends of said elongated body being folded about said central portion to form a cleaning device;

e) each of said distal ends formed as a loop;

f) said padding material in each of said distal ends formed in a loop to define an eyelet;

wherein said eyelet holes are covered by said padded materials.

* * * * *